United States Patent

Iwanaga et al.

Patent Number: 5,868,677
Date of Patent: Feb. 9, 1999

[54] BIOINSTRUMENTATION DEVICE FOR MEASURING A BIOLOGICAL PARAMETER

[75] Inventors: Kusuo Iwanaga; Hiroyuki Inbe, both of Osaka; Izumi Mihara, Daito, all of Japan

[73] Assignee: Matsushita Electric Works, Ltd., Osaka, Japan

[21] Appl. No.: 775,929

[22] Filed: Jan. 2, 1997

[51] Int. Cl.$^6$ ...................................... A61B 5/00
[52] U.S. Cl. ........................ 600/481; 600/529; 600/488
[58] Field of Search .................. 600/342, 529, 600/561, 593, 484, 483, 527, 505, 486, 479, 480, 531, 481, 488, 500

[56] References Cited

U.S. PATENT DOCUMENTS

| | | | |
|---|---|---|---|
| 4,757,194 | 7/1988 | Simms | 600/593 |
| 5,018,529 | 5/1991 | Tenerez et al. | 600/561 |
| 5,178,153 | 1/1993 | Einzig | 600/505 |

*Primary Examiner*—Jennifer Bahr
*Assistant Examiner*—Stephen Huane
*Attorney, Agent, or Firm*—Armstrong, Westerman, Hattori, McLeland & Naughton

[57] ABSTRACT

A bioinstrumentation device utilizes an optical fiber for measuring biological parameters such as heart rate and breathing rate of a human subject. The device utilizes an optical fiber as a sensing element for sensing minute load variations resulting from the heart beating and breathing of the human subject and therefore indicative of the heart rate and the breathing rate. The device includes a base and a movable member movable relative to the base. The movable member is connected to a support structure for the human body and receives the minute load variations from the living body so as to vibrate in response thereto. Disposed between the base and the movable member is the optical fiber which is capable of resiliently deforming with changing characteristic of its internal reflectivity. A light source is disposed adjacent to the input end of the optical fiber to feed a light through the optical fiber. The light emitted from the optical fiber is received by a light sensor disposed adjacent to the output end of the optical fiber. An analyzing circuit is provided to analyze a variation in the amount of the light received at the light sensor due to the changing internal reflectivity of the optical fiber being deformed so as to determine the biological parameter. A retainer structure is included to keep the optical fiber bent with an initial curvature such that the optical fiber is caused to deform with a varying curvature from the initial curvature in response to minute load variations indicative of the biological parameters to be measured.

7 Claims, 7 Drawing Sheets

BIOINSTRUMENTATION DEVICE FOR MEASURING A BIOLOGICAL PARAMETER

BACKGROUND ART

1. Field of the Invention

The present invention is directed to a bioinstrumentation device for measuring a biological parameter of a living body, and more particularly for measuring a heart rate and a breathing rate of a human subject without giving any annoying constriction to the subject.

2. Description of the Prior Art

It has been known in the art to measure a biological parameter such as heart rate and the breathing rate from periodical minute variations or vibrations appearing in the weight of a human subject as a consequence of the heart beat and the breathing of the subject. Japanese Patent Publication No. 6-30914 proposes to use an optical fiber for sensing such minute variations based upon the finding that optical fiber will change its internal reflectivity as it is caused to deform under the influence of the weight or load variations. The change of the internal reflectivity results in corresponding change in the amount of the light transmitted through the optical fiber which can be readily analyzed to determine the heart rate and the breathing rate. However, there still remains a problem to be solved in order to achieve sufficient sensitivity or S/N ratio for accurately determining the heart rate and the breathing rate. The problem concerns that when the optical fiber is kept generally straight, no remarkable change in the reflectivity develops with a slight deformation of the optical fiber from the straight condition, thereby failing to derive a reliable indication of the minute load variations representing the biological parameters.

SUMMARY OF THE INVENTION

In view of the above problem, the present invention has been made to provide an improved bioinstrumentation device which is capable of sensing minute variations in the weight of the living body with the use of an optical fiber and therefore accurately determining the biological parameters of the subject. The device in accordance with the present invention comprises a base and a movable member which is movable relative to the base. The movable member is connected to a support structure for the living body and receives minute load variations from the living body so as to vibrate in response to the minute load variations. Disposed between the base and the movable member is an optical fiber which has an input end and an output end, and which is capable of resiliently deforming with changing characteristic of its internal reflectivity. A light source is disposed adjacent to the input end of the optical fiber to feed a light through the optical fiber. The light emitted from the optical fiber is received by a light sensor disposed adjacent to the output end of the optical fiber. An analyzing circuit is provided to analyze a variation in the amount of the light received at the light sensor due to the changing internal reflectivity of the optical fiber being deformed so as to determine the biological parameters. The device is characterized to include a retainer structure for keeping the optical fiber bent with an initial curvature such that the optical fiber is caused to deform with a varying curvature from the initial curvature in response to the minute load variations applied to said optical fiber from the living body.

Preferably, the device includes a stopper for limiting the relative movement of the movable member to the base to thereby restrict the deformation amount of the optical fiber below a predetermined extent for avoiding break of the optical fiber when subjected to an excess load.

The retainer structure is arranged to increase the curvature with the increasing load. In a preferred embodiment, the retainer structure comprises a plurality of first teeth formed on the base and a plurality of second teeth formed on the movable member. The first and second teeth are arranged to stagger with respect to each other and hold the optical fiber therebetween so that the optical fiber is bent at plural deflection points along its length between the first and second teeth. With this structure, it is possible to increase the rate of change for the light passing through the optical fiber, thereby increasing response sensitivity for accurate measurement of the biological parameters.

The first and second teeth are provided respectively with first and second grooves for receiving therein portions of the optical fiber. Accordingly, the optical fiber can be positioned easily and exactly between the base and the movable member. The first and second groove is formed to have chamfered edges so as not damage the optical fiber. Further, the bottom of the groove is rounded for smooth contact with the optical fiber in order to effectively deform the optical fiber while keeping it intact.

The optical fiber may be curved in a plane perpendicular to a direction in which the load is applied to the optical fiber so that the deflection points of the optical fibers can be densely distributed per unit area so that the device can be sufficiently compact yet realizing high sensitivity.

These and still other objects and advantageous feature of the present invention will become more apparent from the following description of the embodiments when taken in conjunction with the attached drawings.

DETAILED DESCRIPTION OF THE INVENTION

Figure 1:
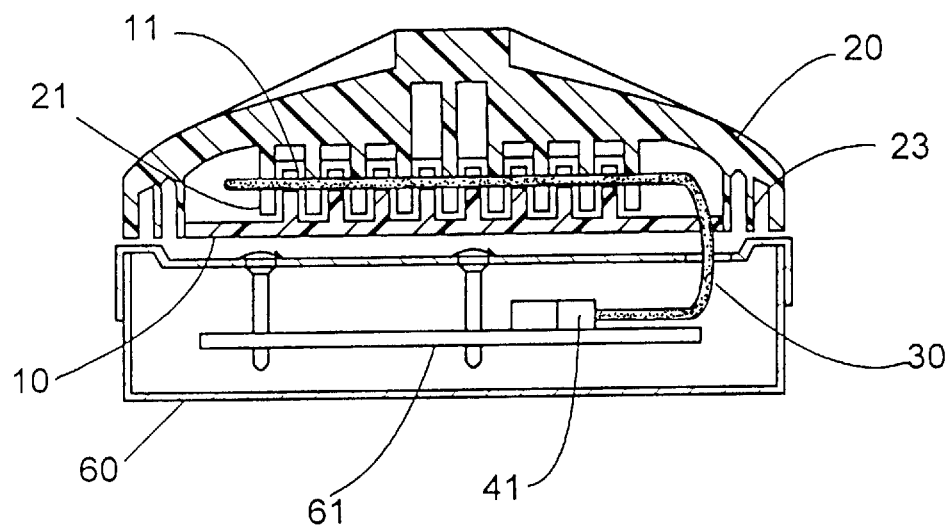
FIG. 1 is a cross sectional view of a bioinstrumentation device in accordance with a preferred embodiment of the present invention.
Figure 2:
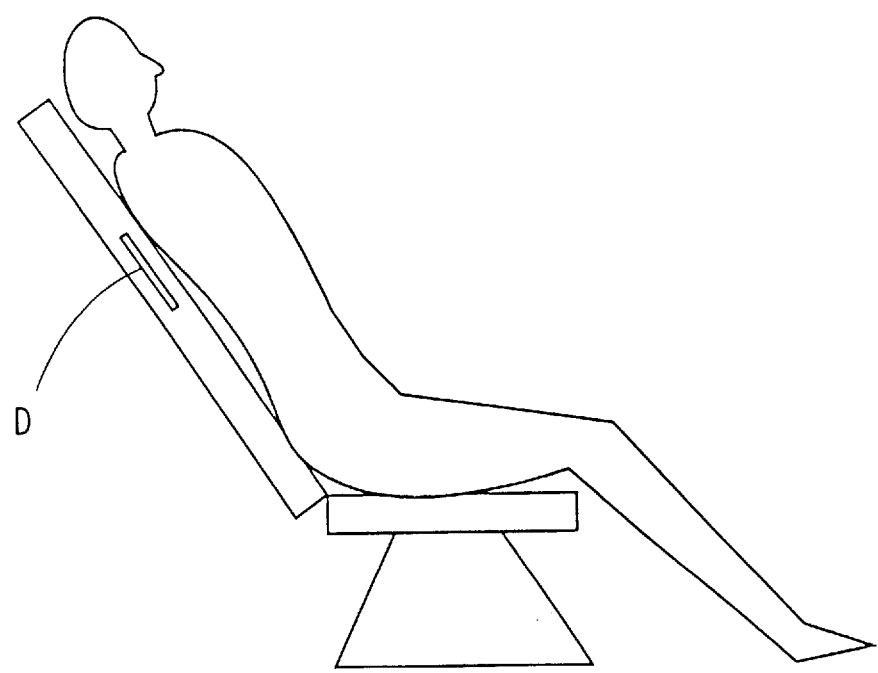
FIG. 2 is a diagram illustrating a chair for which the above device is utilized.

Referring now to FIG. 1, there is shown a bioinstrumentation device D in accordance with the present invention which is incorporated in a chair, for example, as shown in FIG. 2, in order to measure biological parameters such as heart rate and breathing rate of a person sitting on the chair without requiring any annoying constriction to the person. The device comprises a base 10 connected to a supporting structure of the chair and a cover 20 movably mounted in the chair at a portion bearing the person, i.e., the back or bottom thereof. For example, the cover 20 is connected to a spring net disposed behind a cushion of the chair. Thus, the cover 20 is movable relative to the base 10 in response to periodical minute variations or vibrations of load applied to the cover 20 from the person. The periodical minute load variations include information indicative of the biological parameters such as heart rate and breathing rate, or even brain wave which are closely related to the heart rate and the breathing rate.

Figure 5:
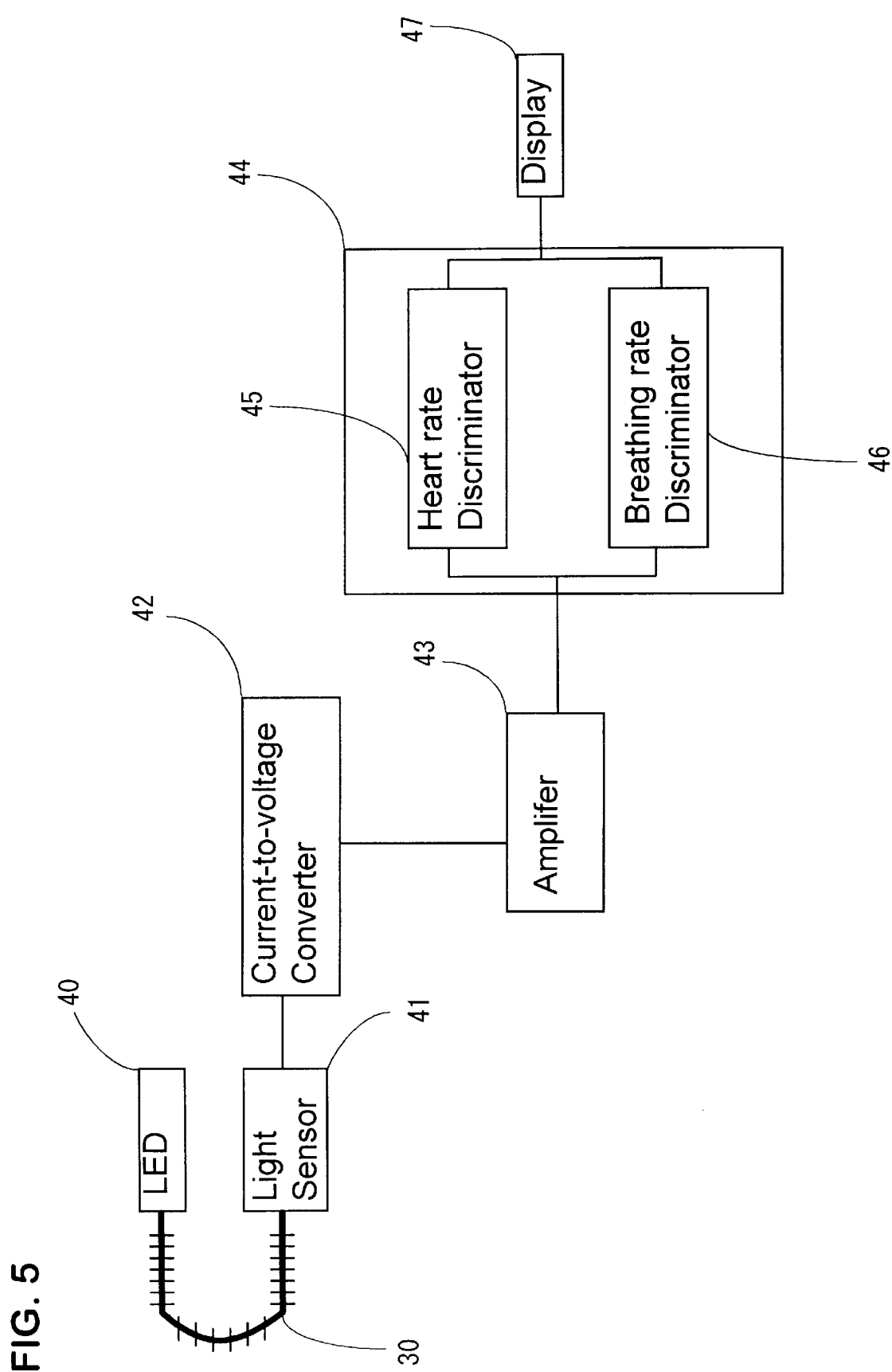
FIG. 5 is a block diagram illustrating a circuit configuration of the device.
Figure 6:
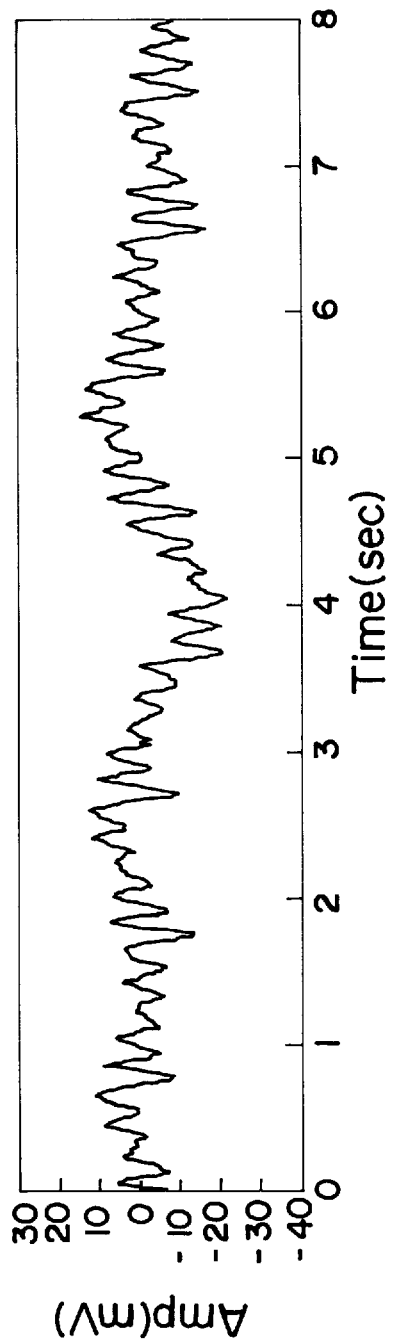
FIG. 6 is a graph illustrating a signal indicative of the biological parameters to be measured by the above device.

Disposed between the base 10 and the cover 20 is a single optical fiber 30 which is capable of resiliently deforming to change its internal reflectivity as the cover 20 moves in response to the periodical minute load variations. That is, as the optical fiber 30 is deformed, the total internal reflectance is broken at portions being critically deformed to thereby reduce the amount of the light being transmitted through the length of the optical fiber 30. A light source 40 in the form of a light emitting diode (LED) is disposed in juxtaposition to an input end of the optical fiber 30 to feed the light therethrough. A light sensor 41 is disposed in juxtaposition to an output end of the optical fiber 30 to receive the light emitted from the optical fiber 30. Thus, the above reduction in the amount of the light is known from an output of the light sensor 41. As shown in FIG. 5, the output of the light sensor 41 is fed through a current-to-voltage converter 42 followed by being amplified at an amplifier 43 to give a corresponding voltage signal Vs, as shown in FIG. 6. The voltage signal Vs is then fed to an analyzing circuit 44 where it is analyzed to determine a heart rate and a breathing rate respectively at a heart rate discriminator 45 and a breathing rate discriminator 46. The heart rate is represented by a high frequency component superimposed on the voltage signal Vs and can be derived by the use of a low-pass filter, while the breathing rate is represented by a low frequency component of the voltage signal Vs and can be therefore derived by the use of a high-pass filter. Thus determined biological parameters are selectively or simultaneously shown at a display 47 to be seen by the user. Alternatively, thus determined biological parameters can be utilized for a feedback control of stimulating the user for treatment of physical or psychological disorders.

Figure 3:
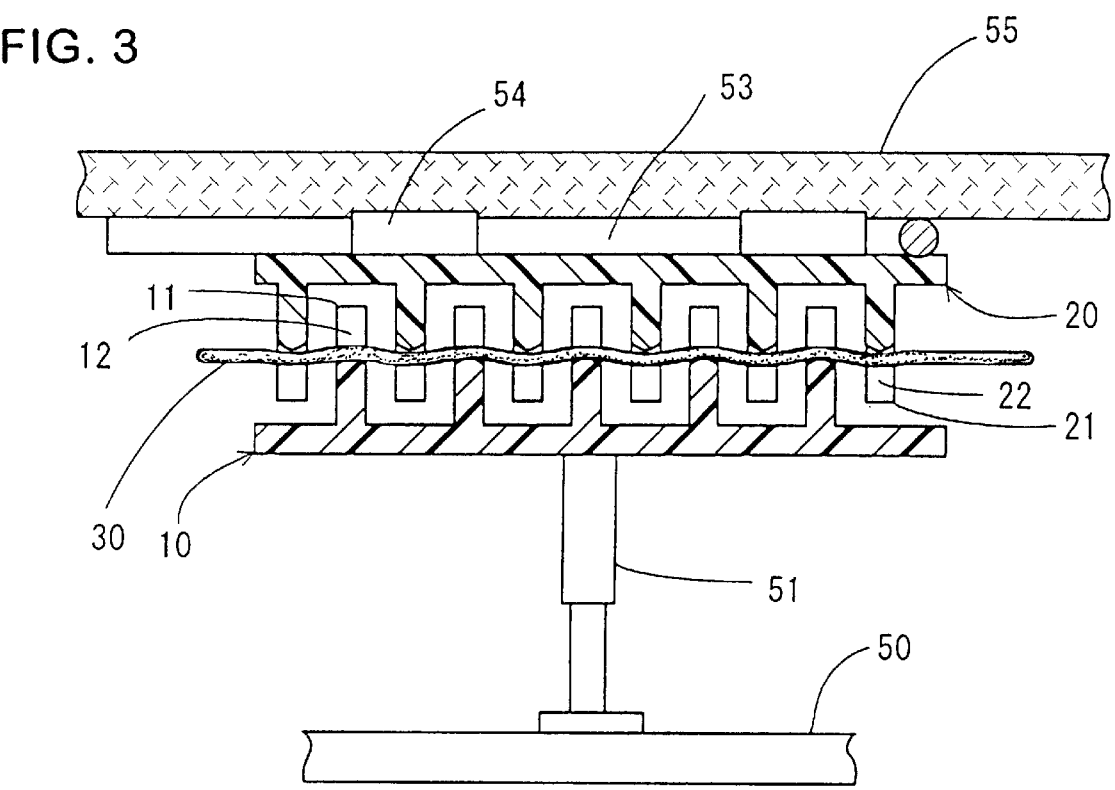
FIGS. 3 and 4 are sectional views illustrating the operation of the device.
Figure 4:
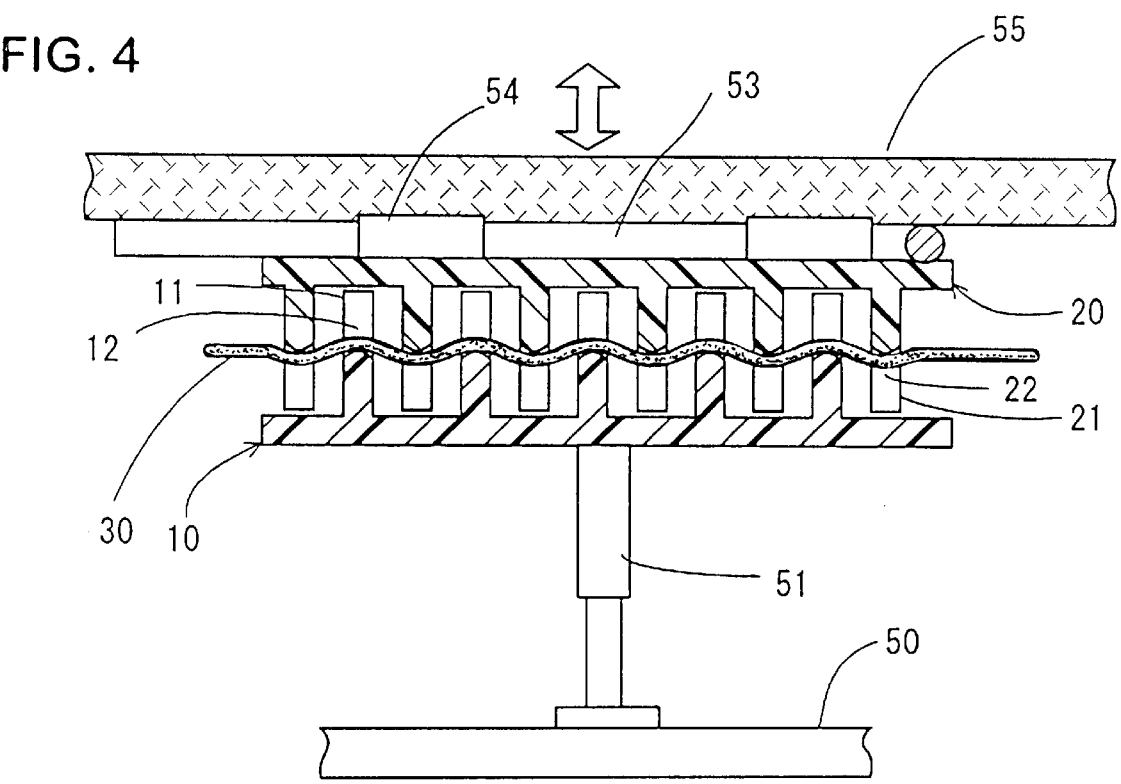

The optical fiber 30 is selected to have enough resiliency to be capable of resiliently deforming with changing internal reflectivity in response to the minute load variations and comprises about 1.0 mm diameter core of acrylic resin and about 0.6 mm thick clad of cross-linked polyethylene. The optical fiber 30 is arranged to deform at plural deflection points along its length in response to the minute load variations. Also, the optical fiber 30 is kept bent at the plural deflection points even in the absence of the load of the user, as typically shown in FIG. 3, so as to have an initial curvature at the respective plural deflection points where the total internal reflectance is assumed to be partly broken to such an extent that a further deformation will cause remarkable change in the internal reflectivity of the optical fiber 30. As shown in FIG. 4, the optical fiber 30 is caused to further deformed with increasing curvature as the minute load is applied thereto through the cover 20.

Figure 7:
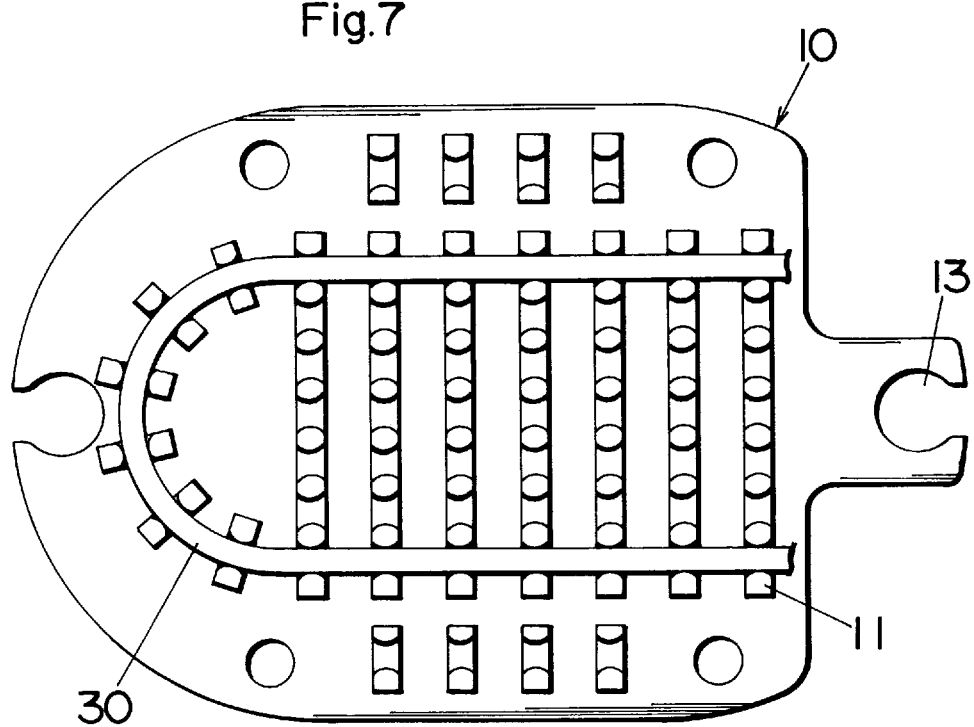
FIG. 7 is a plan view of a base of the device.
Figure 8:
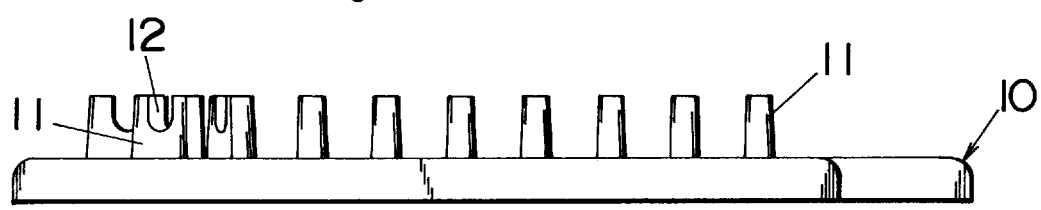
FIG. 8 is a side view of the base.
Figure 9:
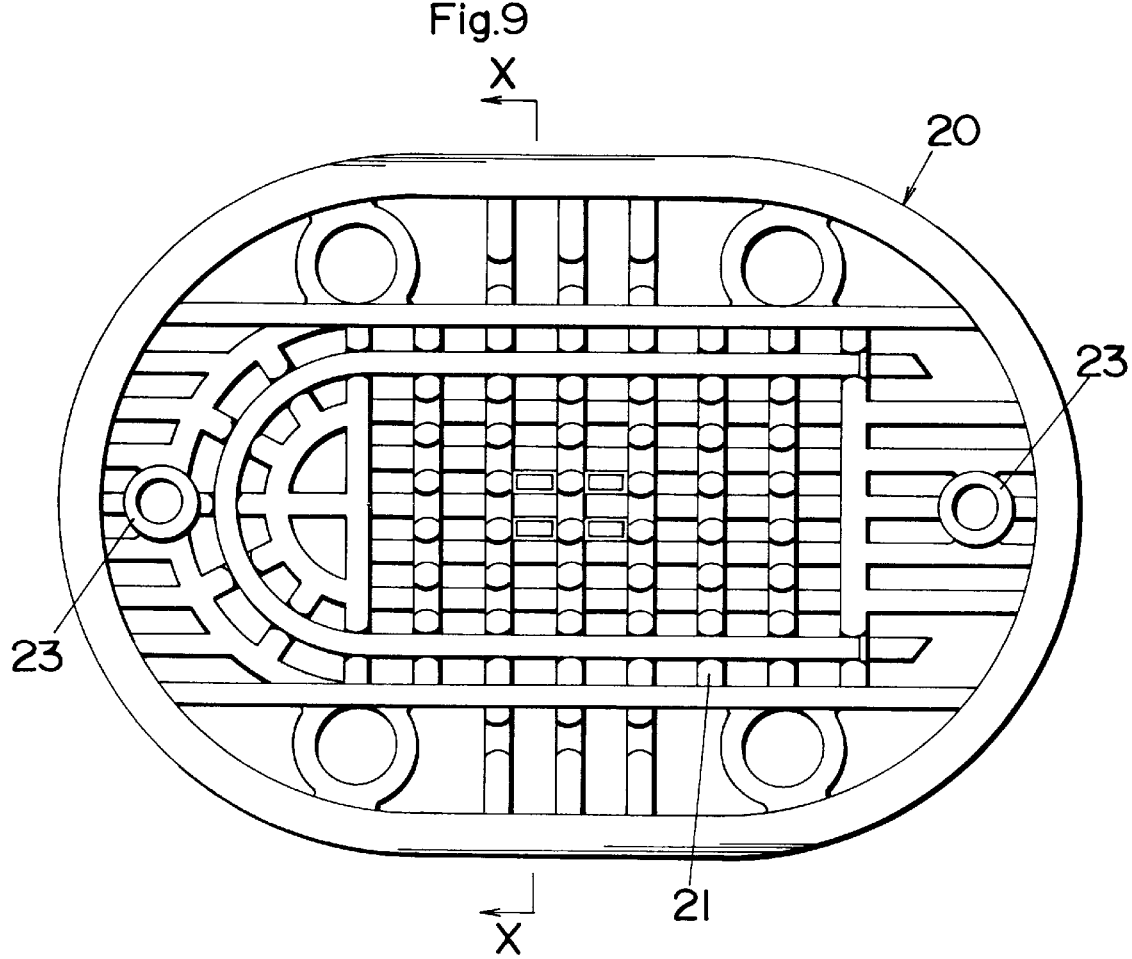
FIG. 9 is a bottom view of a cover fitted on the base of the device.
Figure 10:
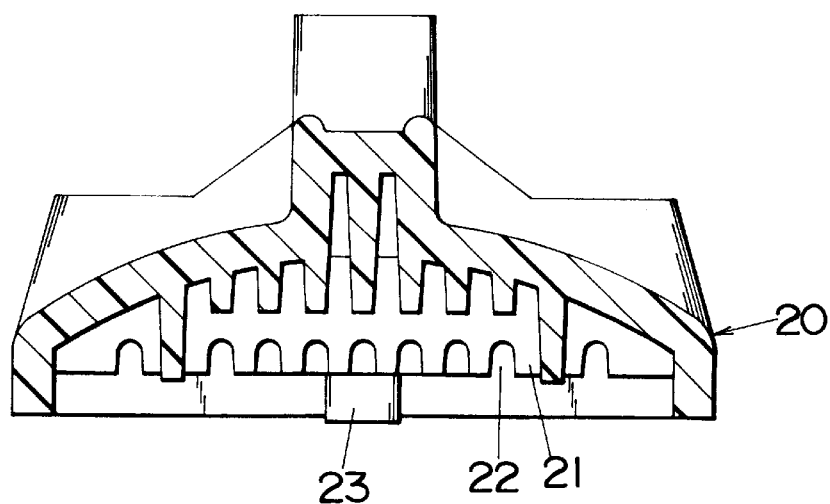
FIG. 10 is a sectional view taken along X—X of FIG. 9.

The base 10 and the cover 20 are molded from a hard plastic material to have a plurality of first and second teeth 11 and 21 which are staggered with respect to each other to hold therebetween the optical fiber 30. Each of the first and second teeth 11 and 21 is formed with each one of first and second groove 12 and 22 for receiving therein the portions of the optical fibers, as shown in FIGS. 3 and 4. The edges of the first and second grooves 12 and 22 are chamfered to avoid damaging the optical fiber 30. That is, the bottoms of the grooves are rounded. The tips of the first and second teeth 11 and 12 define stoppers which abut against the cover 20 and the base 10, respectively to limit the relative movement of the cover 20 to the base 10, i.e., avoid excess deformation of the optical fiber 30. As shown in FIGS. 7 and 8, the base 10 is in the form of a flat plate integrally molded with the first teeth 11. The first grooves 12 of the first teeth 11 are arranged along a U-shaped line to hold the optical fiber 30 curved in the U-shaped fashion within a horizontal plane perpendicular to a direction in which the minute load variations is applied to the optical fiber 30. The pitch of the first teeth 11 along the U-shaped line is selected to be 7 mm. As shown in FIGS. 9 and 10, the cover 20 is in the form of a shallow cap integrally molded with the second teeth 21 projecting on the bottom of the cap. The second grooves 22 of the second teeth 21 are arranged in correspondence to the first grooves to hold the optical fiber 30 in the U-shaped in cooperation with the first grooves 12. The pitches of the second teeth 21 are also 7 mm. The base 10 and the cover 20 are formed with a number of first and second teeth which are not responsible for holding the optical fiber 30 but act as the stoppers as mentioned in the above. Such plural stoppers are distributed generally evenly so as to bear a strong load which may be applied when a heavy weight user sits down on the chair violently for protection of the optical fiber even against unexpectedly great load. The base 10 is fitted in the opening of the cap 20 by slidable engagement of studs 23 at the end of the cap 20 into holes 13 of the base 10. The base 10 is connected to the supporting structure 50 through a dampener 51 which absorbs abrupt change of the load to thereby allow the base 10 to move by a macro displacement but to hold the base 10 fixed against the minor load variations applied to the cover 20. Also, the dampener 51 is configured to apply a pressure of 4 kg in order to pre-stress or deform the optical fiber at the initial curvature in the absence of the user such that a further deformation of the optical fiber results in remarkable change in the amount of the light passed through the optical fiber for enhancing sensitivity or S/N ratio to the minute load variations indicative of the biological parameters. The maximum deformation is restricted to the curvature corresponding to 0.5 mm deflection of the optical fiber by the stoppers defined by the first and second teeth 11 and 21. The cover 10 is secured to a spring net 52 by clasps 54 behind a cushion 55 of the chair. The spring net 52 is connected to the supporting structure of the chair and vibrates in response to the minute load variations and therefore transmits the same to periodically move the cap 20, i.e., periodically deform the optical fiber 30, which generates the signal truly indicative of the heart rate and the breathing rate.

Turning back to FIG. 1, a case 60 is mounted below the base 10 to be movable together therewith. Accommodated in the case 60 is electronic components which are mounted on a circuit board 61 to realize the circuit of FIG. 5 including LED 40, light sensor 41, current-to-voltage converter 42, and analyzing circuit 44.

Figure 11:
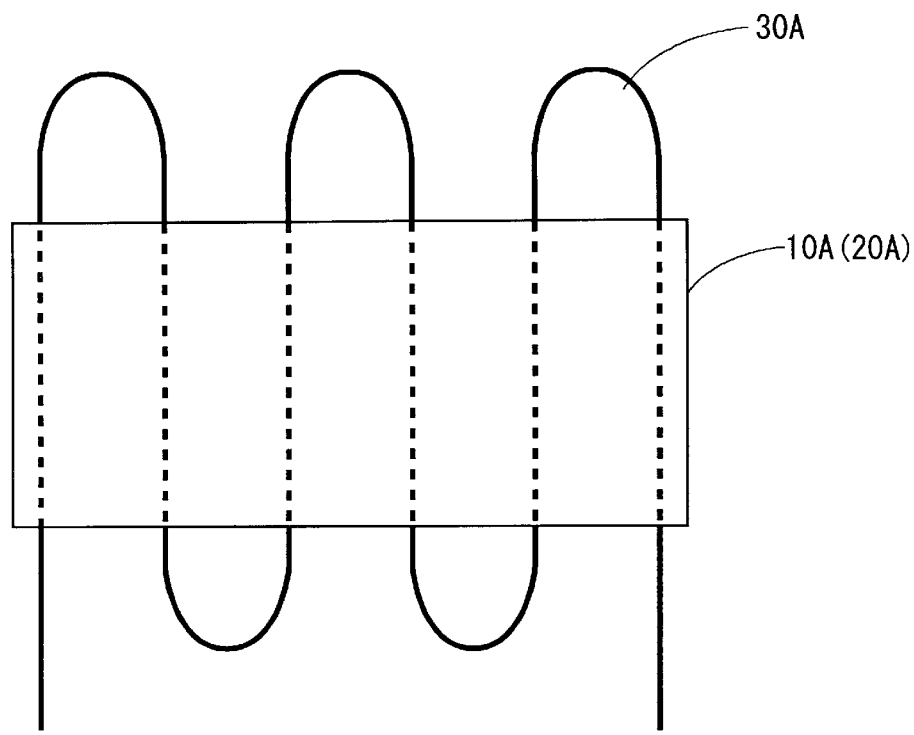
FIGS. 11 and 12 are schematic views illustrating modified arrangements of an optical fiber utilized in the above device.
Figure 12:
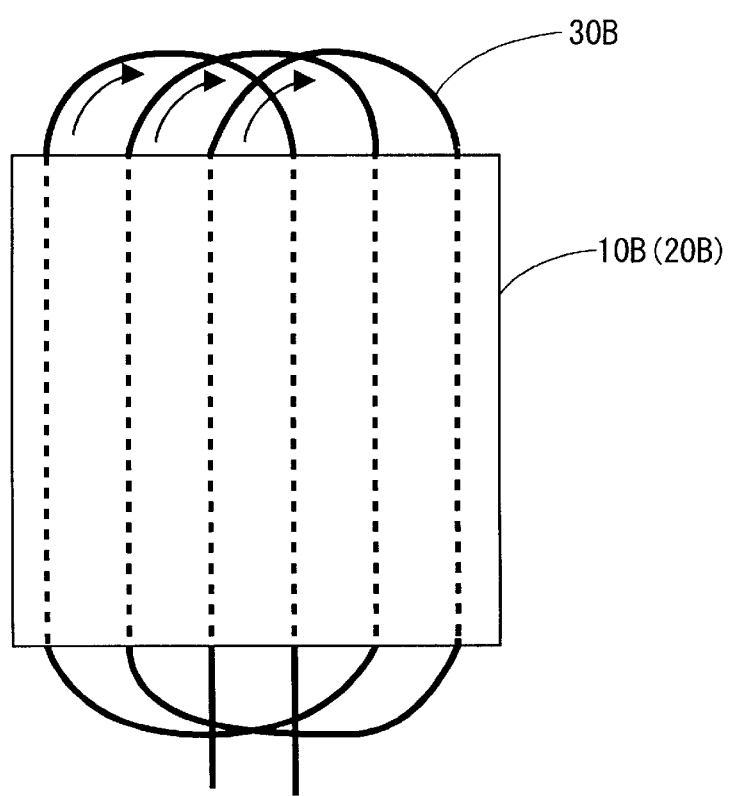

Although the above embodiment illustrates the U-shaped arrangement of the optical fiber 30, the present invention should not be limited thereto and may include modified arrangements of FIGS. 11 and 12. FIG. 11 illustrates an optical fiber 30A which is curved in the same plane to have a plurality of turns 34 connected by straight segments 35. The straight segments 35 are held between the like teeth of a base and a cover 10A (20A) to have plural deflection points at which the optical fiber is caused to deform. The modification of FIG. 12 shows an optical fiber 30B which is curved substantially in the horizontal plane to have a plurality of elongated loops with straight segments 35B. The straight segments 35B are held between the like teeth of a base and a cover 10B (20B) to have plural deflection points at which the optical fiber 30B is caused to deform. The loops are partly overlapped to arrange the straight segments 35B in closely adjacent relation, thereby enabling to make the whole device compact while increasing the number of deflection points along the length of the optical fiber 30B and therefore enhancing capability of detecting the minute load variations within a limited space.

What is claimed is:

1. A bioinstrumentation device for measuring a biological parameter of a living body, said device comprises:

a base;

a movable member which is movable relative to said base, said movable member being connected to a support structure for the living body and receives periodical minute load variations from the living body so as to vibrate in response to said minute load variations;

an optical fiber having an input end and an output end, said optical fiber being disposed between said base and movable member to be capable of resiliently deforming commensurate with changing characteristic of its internal reflectivity;

a light source disposed adjacent to said input end of said optical fiber to feed a light through said optical fiber;

a light sensor disposed adjacent to said output end of said optical fiber to receive the light emitted from said optical fiber;

analyzing means which analyzes a variation in amount of the light received at said light sensor due to the changing internal reflectivity of said optical fiber being deformed so as to determine said biological parameter; and retainer means for keeping said optical fiber bent with an initial curvature before the optical fiber receives a load from the subject such that said optical fiber is caused to resiliently deform with a varying curvature from said initial curvature in response to said minute load variations.

2. The bioinstrumentation device as set forth in claim 1, wherein said retainer means is arranged to increase the curvature of said optical fiber with increasing load.

3. The bioinstrumentation device as set forth in claim 2, further including stopper means for limiting relative movement of said movable member to said base to thereby restrict the deformation amount of said optical fiber below a predetermined extent.

4. The bioinstrumentation device as set forth in claim 2, wherein said retainer means comprises a plurality of first teeth formed on said base and a plurality of second teeth formed on said movable member, said first and second teeth being arranged to stagger with respect to each other and holding said optical fiber therebetween so that said optical fiber is bent at plural points along its length between said first and second teeth.

5. The bioinstrumentation device as set forth in claim 4, wherein said first and second teeth are provided respectively with first and second grooves for receiving therein portions of said optical fiber.

6. The bioinstrumentation device as set forth in claim 5, wherein each of said first and second grooves is formed to have chamfered edges.

7. The bioinstrumentation device as set forth in claim 4, wherein said optical fiber is curved in a plane perpendicular to a direction in which said load is applied to the optical fiber.

* * * * *